United States Patent
Liron et al.

(10) Patent No.: US 12,059,266 B2
(45) Date of Patent: Aug. 13, 2024

(54) SYSTEM AND METHOD FOR ARRHYTHMIA DETECTION DURING AN AT HOME SLEEP TEST

(71) Applicant: Itamar Medical, Ltd., Caesarea (IL)

(72) Inventors: Guy Liron, Haifa (IL); Efrat Litman, Tel-Aviv (IL); Ravit Roytman, Herzliya (IL)

(73) Assignee: Itamar Medical Ltd., Caesarea (IL)

( * ) Notice: Subject to any disclaimer, the term of this patent is extended or adjusted under 35 U.S.C. 154(b) by 158 days.

(21) Appl. No.: 17/381,752

(22) Filed: Jul. 21, 2021

(65) Prior Publication Data

US 2022/0202359 A1    Jun. 30, 2022

Related U.S. Application Data

(60) Provisional application No. 63/131,919, filed on Dec. 30, 2020.

(51) Int. Cl.
*A61B 5/00* (2006.01)
*A61B 5/0205* (2006.01)
(Continued)

(52) U.S. Cl.
CPC .......... *A61B 5/4818* (2013.01); *A61B 5/0205* (2013.01); *A61B 5/02116* (2013.01); *A61B 5/02405* (2013.01); *A61B 5/02416* (2013.01); *A61B 5/08* (2013.01); *A61B 5/14542* (2013.01); *A61B 5/4809* (2013.01)

(58) Field of Classification Search
CPC . A61B 5/4818; A61B 5/0205; A61B 5/02116; A61B 5/02405; A61B 5/02416; A61B 5/08; A61B 5/14542; A61B 5/4809
See application file for complete search history.

(56) References Cited

U.S. PATENT DOCUMENTS 6,319,205 B1    11/2001    Goor et al.
6,461,305 B1    10/2002    Schnall
(Continued)

FOREIGN PATENT DOCUMENTS

DE    102019104798 A1    10/2019
WO   WO-2021260192 A1 *  12/2021
WO   WO-2022048871 A1 *   3/2022

OTHER PUBLICATIONS

Li et al., "Probability density distribution of delta RR intervals: a novel method for the detection of atrial fibrillation", Australasian Physical & Engineering Sciences in Medicine, 2017, pp. 707-716, vol. 40.

(Continued)

*Primary Examiner* — Aaron F Roane
(74) *Attorney, Agent, or Firm* — The Webb Law Firm

(57) ABSTRACT

A method and system for detecting atrial fibrillations from a photoplethysmogram (PPG) signal. A method includes continuously generating a PPG signal measurement from a sensor of a PPG unit; generating a plurality of time frame samples based on the PPG signal measurement; generating, for each time frame sample, a plurality of heart rate (RR) intervals; determining an RR interval distribution for each time frame sample based on the plurality of RR intervals; and detecting at least one atrial fibrillation event based on the RR interval distribution for each time frame sample.

26 Claims, 11 Drawing Sheets

(51) Int. Cl.
    *A61B 5/021*     (2006.01)
    *A61B 5/024*     (2006.01)
    *A61B 5/08*     (2006.01)
    *A61B 5/145*     (2006.01)

(56) References Cited

U.S. PATENT DOCUMENTS

| | | |
|---|---|---|
| 6,916,289 B2 | 7/2005 | Schnall |
| 6,939,304 B2 | 9/2005 | Schnall et al. |
| 7,374,540 B2 | 5/2008 | Schnall |
| 7,806,831 B2 | 10/2010 | Lavie et al. |
| 2017/0156593 A1 | 6/2017 | Ferber et al. |
| 2018/0064388 A1* | 3/2018 | Heneghan ............. A61B 5/1114 |
| 2018/0146870 A1* | 5/2018 | Shemesh ............ A61B 5/02416 |
| 2018/0279891 A1* | 10/2018 | Miao ................. A61B 5/02416 |
| 2019/0099125 A1 | 4/2019 | Schnall |
| 2019/0298208 A1* | 10/2019 | Weinstein .......... A61B 5/02438 |
| 2020/0043591 A1* | 2/2020 | Kahlert .................. G16H 20/30 |
| 2020/0100693 A1* | 4/2020 | Velo ........................ A61B 5/746 |
| 2021/0022667 A1* | 1/2021 | Sayadi ................ A61B 5/4806 |

OTHER PUBLICATIONS

Shan et al., "Reliable PPG-based Algorithm in Atrial Fibrillation Detection", 2016 IEEE Biomedical Circuits and Systems Conference (BioCAS), 2016, pp. 340-343.

Yoon et al., "Slow-wave Sleep Estimation for Healthy Subjects and OSA Patients Using R-R Intervals", IEEE Journal of Biomedical and Health Informatics, 2017, pp. 119-128.

* cited by examiner

SYSTEM AND METHOD FOR ARRHYTHMIA DETECTION DURING AN AT HOME SLEEP TEST

CROSS-REFERENCE TO RELATED APPLICATIONS

This application claims the benefit of U.S. Provisional Application No. 63/131,919 filed on Dec. 30, 2020, the contents of which are hereby incorporated by reference.

TECHNICAL FIELD

The disclosure generally relates to arrythmia detection and specifically to arrhythmia detection using a photoplethysmogram signal.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Similarly, issues identified with respect to one or more approaches should not assume to have been recognized in any prior art on the basis of this section, unless otherwise indicated.

Recently, arrhythmia events exhibited during sleep have become of interest to cardiologists, as a connection has been found between sleep disorders and cardiac events in general, and sleep apnea with arrhythmia and atrial fibrillations (Afib) in particular.

Patients may spend between a quarter to a full third of their day sleeping, and with the strong comorbidity between sleep disorders and cardiac events, it may be especially beneficial to be able to provide data and insights to monitoring physicians. Even more so when patients having conditions such as Afib may be asymptomatic and unaware of a potentially life-threatening condition.

It is therefore beneficial to provide additional medical information regarding a patient's health, in order to at least improve patient care.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "certain embodiments" may be used herein to refer to a single embodiment or multiple embodiments of the disclosure.

Certain embodiments disclosed herein include method for detecting atrial fibrillations from a photoplethysmogram (PPG) signal. The method comprises continuously generating a PPG signal measurement from a sensor of a PPG unit; generating a plurality of time frame samples based on the PPG signal measurement; generating, for each time frame sample, a plurality of heart rate (RR) intervals; determining an RR interval distribution for each time frame sample based on the plurality of RR intervals; and detecting at least one atrial fibrillation event based on the RR interval distribution for each time frame sample.

Certain embodiments disclosed herein also include a non-transitory computer readable medium having stored thereon causing a processing circuitry to execute a process, the process comprising: continuously generating a PPG signal measurement from a sensor of a PPG unit; generating a plurality of time frame samples based on the PPG signal measurement; generating, for each time frame sample, a plurality of heart rate (RR) intervals; determining an RR interval distribution for each time frame sample based on the plurality of RR intervals; and detecting at least one atrial fibrillation event based on the RR interval distribution for each time frame sample.

Certain embodiments disclosed herein also include a system for detecting atrial fibrillations from a photoplethysmogram (PPG) signal. The system comprises: a processing circuitry; and a memory, the memory containing instructions that, when executed by the processing circuitry, configure the system to: continuously generate a PPG signal measurement from a sensor of a PPG unit; generate a plurality of time frame samples based on the PPG signal measurement; generate, for each time frame sample, a plurality of heart rate (RR) intervals; determine an RR interval distribution for each time frame sample based on the plurality of RR intervals; and detect at least one atrial fibrillation event based on the RR interval distribution for each time frame sample.

Certain embodiments disclosed herein also include a method for detecting atrial fibrillations from a photoplethysmogram (PPG) signal, comprising: continuously generating a PPG signal measurement from a sensor of a PPG unit; generating a plurality of time frame samples based on the PPG signal measurement; generating, for each time frame sample, a plurality of heart rate (RR) intervals; determining an RR interval distribution for each time frame sample based on the plurality of RR intervals; detecting at least one atrial fibrillation event based on the RR interval distribution for each time frame sample; determining an average pulse rate for each time frame sample; and detecting a tachycardia event based on a time frame sample having an average pulse rate above a predetermined threshold.

Certain embodiments disclosed herein also include a method for detecting atrial fibrillations from a photoplethysmogram (PPG) signal, comprising: continuously generating a PPG signal measurement from a sensor of a PPG unit; generating a plurality of time frame samples based on the PPG signal measurement; generating, for each time frame sample, a plurality of heart rate (RR) intervals; determining an RR interval distribution for each time frame sample based on the plurality of RR intervals; detecting at least one atrial fibrillation event based on the RR interval distribution for each time frame sample; determining an average pulse rate for each time frame sample; and detecting a bradycardia event based on a time frame sample having an average pulse rate below a predetermined threshold.

Certain embodiments disclosed herein also include a method for detecting atrial fibrillations from a photoplethysmogram (PPG) signal, comprising: continuously generating a PPG signal measurement from a sensor of a PPG unit; generating a plurality of time frame samples based on the PPG signal measurement; generating, for each time frame sample, a plurality of heart rate (RR) intervals including a first RR interval and a second RR interval; determining an RR interval distribution for each time frame sample based on the plurality of RR intervals; detecting at least one atrial fibrillation event based on the RR interval distribution for each time frame sample; detecting, based on the PPG signal measurement, a pulse pattern having a reduced amplitude, wherein the pulse pattern is in a first time frame sample of the plurality of time frame samples, wherein the second RR interval of the first time frame sample has a lower amplitude than the first RR interval of the first time frame sample; and detecting a premature heartbeat based on the detected pulse pattern.

Certain embodiments disclosed herein also include a method for detecting atrial fibrillations from a photoplethysmogram (PPG) signal, comprising: continuously generating a PPG signal measurement from a sensor of a PPG unit; generating a plurality of time frame samples based on the PPG signal measurement; generating, for each time frame sample, a plurality of heart rate (RR) intervals including a first RR interval; determining an RR interval distribution for each time frame sample based on the plurality of RR intervals; detecting at least one atrial fibrillation event based on the RR interval distribution for each time frame sample; and detecting a premature heartbeat based on the first RR interval exceeding a predetermined threshold, wherein the predetermined threshold is determined based on a plurality of RR intervals in the time frame sample.

BRIEF DESCRIPTION OF THE DRAWINGS

The subject matter of the disclosure is particularly pointed out and distinctly claimed in the claims at the conclusion of the specification. The foregoing and other objects, features and advantages will become apparent and more readily appreciated from the following detailed description taken in conjunction with the accompanying drawings.

DETAILED DESCRIPTION

Figure 1:
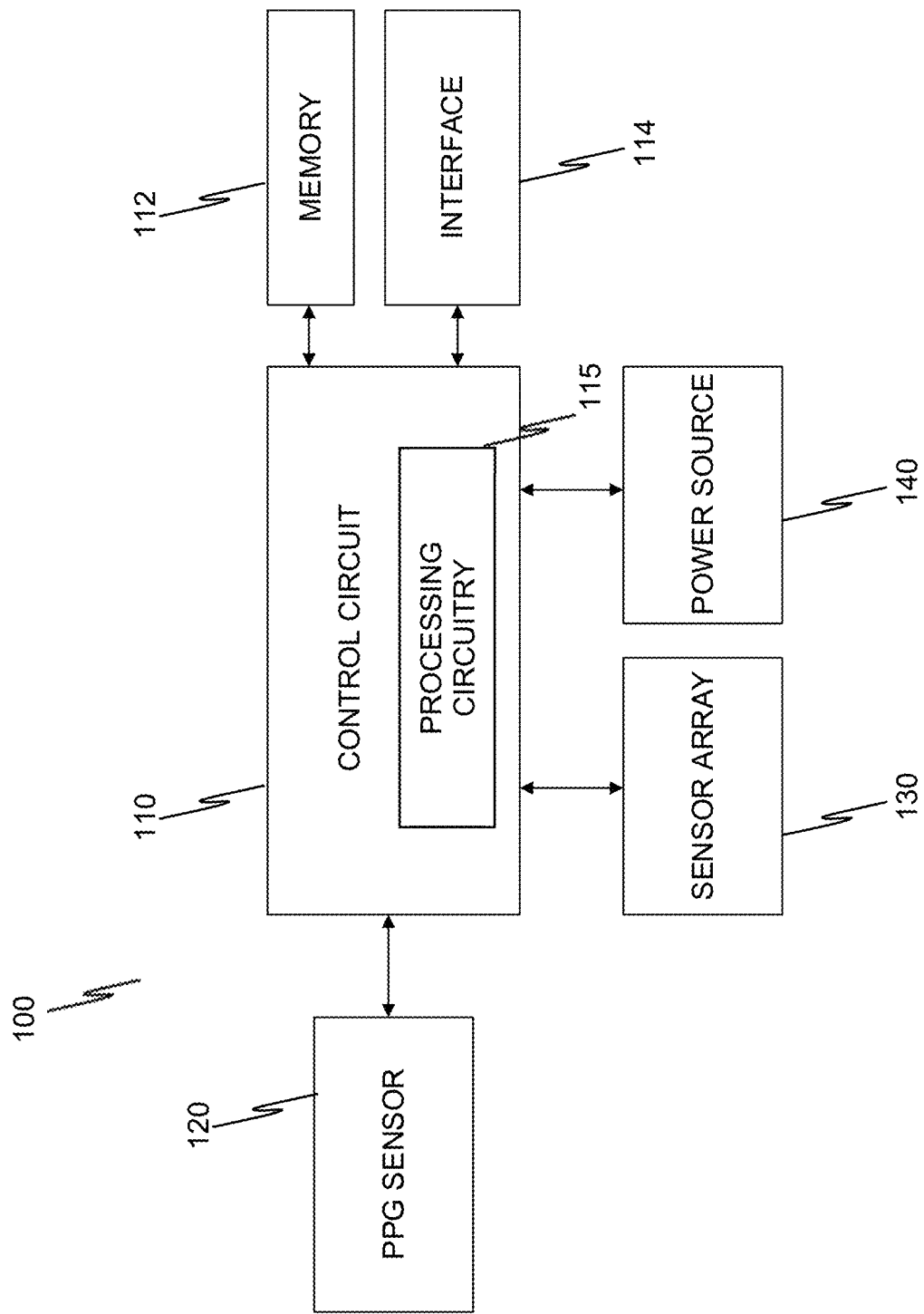
FIG. 1 is a schematic illustration of a photoplethysmogram (PPG) unit according to an embodiment.

Below, embodiments will be described in detail with reference to accompanying drawings so as to be easily realized by a person having ordinary knowledge in the art. The embodiments may be embodied in various forms without being limited to the examples set forth herein. Descriptions of well-known parts are omitted for clarity, and like reference numerals refer to like elements throughout.

It is important to note that the embodiments disclosed herein are only examples of the many advantageous uses of the innovative teachings herein. In general, statements made in the specification of the present application do not necessarily limit any of the various claims. Moreover, some statements may apply to some inventive features but not to others. In general, unless otherwise indicated, singular elements may be in plural and vice versa with no loss of generality. In the drawings, like numerals refer to like parts through several views.

A photoplethysmogram (PPG) unit generates a PPG signal, for example from a finger, for the purpose of conducting an at home sleep apnea test. In an embodiment, a peripheral arterial tone (PAT) signal is generated, by applying a static uniform pressure field to the monitored volume. Based on the generated PPG signal, the system monitors for arrhythmia events and apnea events. Arrhythmia events may be determined for example by generating heart rate (RR) intervals from the PPG signal and deriving at least delta-RR values, where delta is the change in the values. Histograms of the RR intervals and delta-RR values having a wide unimodal distribution are indicative of atrial fibrillation. In some embodiments, delta-delta RR values may also be determined and utilized to detect atrial fibrillation. A report may be generated which visually represents detected arrhythmia and apnea events to indicate a correlation between apnea and cardiac events.

FIG. 1 is a schematic illustration of a photoplethysmogram (PPG) unit 100 according to an embodiment. The PPG unit 100 includes a control circuit 110 for controlling and connecting the various elements of the PPG unit 100. In an embodiment, the control circuit 110 includes a processing circuitry 115. The control circuit 110 may include, or be connected to, a memory 112 and an interface 114. In an embodiment, the interface 114 may be a network interface controller (NIC) for providing wired or wireless communication between the control circuit 110 and a network. In other embodiments, the interface may be a data cable used to transmit measurements generated from sensors of the PPG unit 100 to another device.

The control circuit 110 is coupled with a PPG sensor 120, which includes a photoemitter and photosensor (not shown). The control circuit 110 may be further coupled with a sensor array 130, which includes one or more additional sensors such as, but not limited to, position sensors, accelerometers, acoustic sensors, actigraphs, combinations thereof, and the like. In some embodiments, the PPG sensor 120 is positioned in a uniform pressure field (not visually depicted), and the resulting PPG signal is a peripheral arterial tone (PAT) signal.

The control circuit 110 is further coupled with a power source 140, such as a battery, which powers the PPG unit 100. The power source 140 may be single use, multiple use (e.g., rechargeable battery) or operative when connected to a main power supply.

Figure 2:
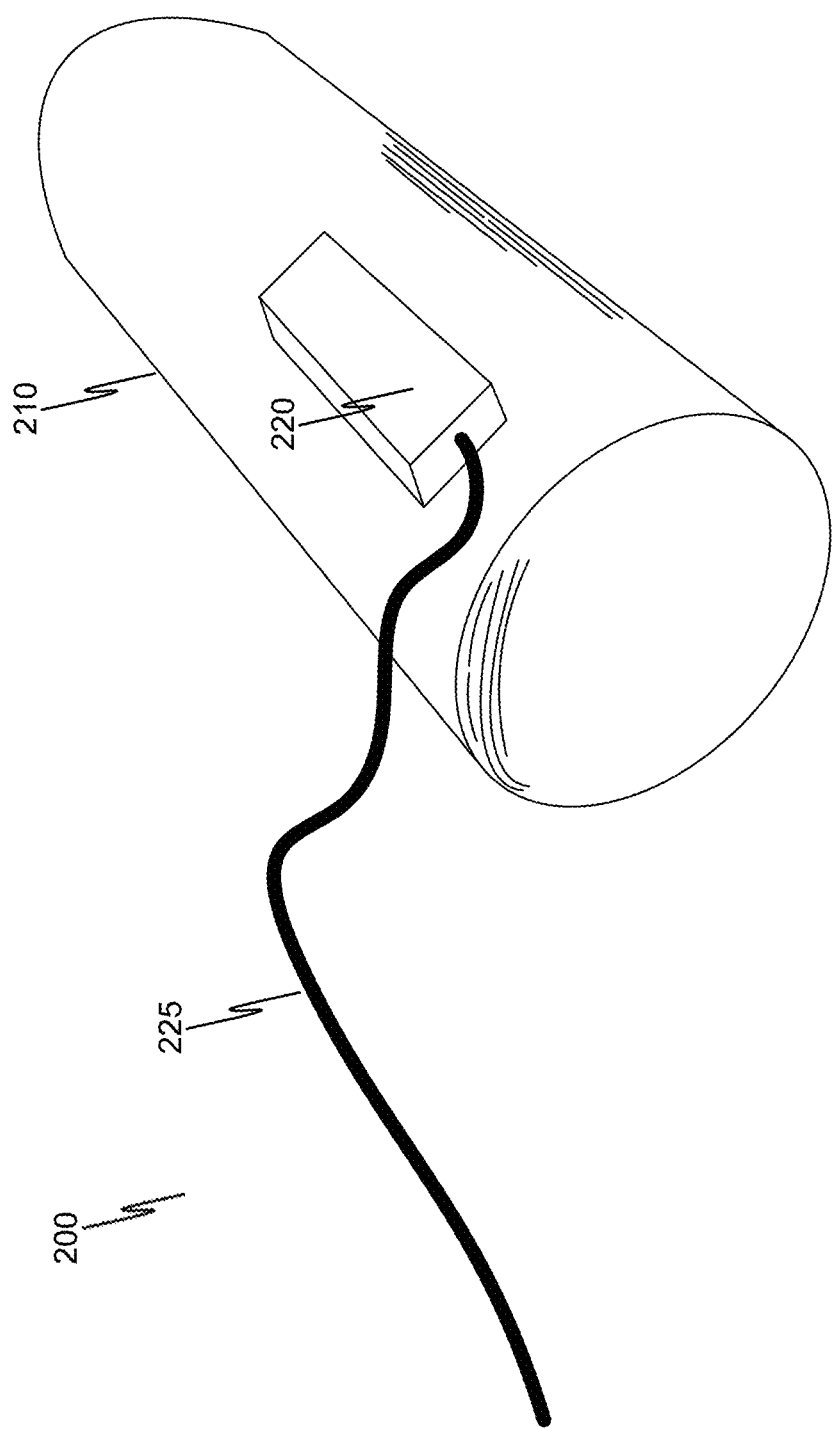
FIG. 2 is a schematic illustration of a PPG unit according to another embodiment.

FIG. 2 is a schematic illustration of a PPG unit 200 implemented according to another embodiment. The PPG unit 200 includes a finger probe housing 210, in which a photosensor and a photoemitter (not shown) may be placed. The finger probe housing 210 houses therein a uniform pressure field (not visually depicted) into which a finger is placed while PPG measurements are generated. A nonlimiting example of such a PPG unit 200 is described in more detail in U.S. Pat. No. 6,916,289 to Schnall et al. assigned to the common assignee, the contents of which are hereby incorporated by reference.

The uniform pressure field is static and, when used with a PPG unit 200, produces a peripheral arterial tone (PAT) signal which is more precise than conventional PPG signals. In some embodiments, a plurality of photoemitters, a plurality of photosensors, or both, may be implemented. In order to apply a sensor to an appendage such as a finger, some sort of pressure needs to be constantly applied so that the sensor does not move. Alternatively, adhesives can be used to secure the sensor in place, or apply contact positioning sensors using, for example, a wristband of a watch. However these methods may be less effective as adhesives can deteriorate, and contacts can be loosened due to motion or even temperature. A mobile sensor may provide indeterminate results, as the PPG signal is influenced by local physiology. However, applying pressure also constricts the blood vessels, thereby affecting the measurement which is the PPG signal. Venous blood is arbitrarily and unpredictably shifted and pooled in the finger's pulp. Therefore, any attempt to measure volume and/or pressure changes will be affected by the signals generated by the venous pooling, which may override and/or offset the desired signals generated by the arterial pressure waves, seriously distorting the actual measurements.

An applied static pressure field should prevent pooling of venous blood in the distal end of the finger, but allow pulsatile blood delivered by the arteries to be returned via the veins. That is, the pressure should be sufficient to prevent free venous flow due to, for example, hydrostatic pressure and shock waves, but allow the veins to carry blood delivered by the arteries out of the finger. The pressure required to prevent venous pooling may differ from person to person.

In order to obtain a clearer signal, the pressure should also be sufficient to partially unload the wall tension of, but not to occlude, the finger arteries when the finger is near heart level. This allows the arterial wall to move freely to accommodate the pulsatile blood delivery of the heart. The applied pressure may be slightly above the maximum pressure in the veins when the hand is fully lowered.

This feature is further advantageous when used in conjunction with a sleep study, as the patient is not cognizant of their movements during sleep and may otherwise dislodge the sensor.

Some existing solutions are susceptible to user movements, and therefore cannot take an accurate measurement when a user is not still. For example, some models of the Apple® Watch require that a user be still for 30 seconds while attempting arrythmia detection utilizing a method of single lead electrocardiogram (ECG). This is a problem, as users are not naturally still, and therefore it is difficult to generate continuous measurements. The disclosed embodiments allow a user to move during performance of measurements while still achieving accurate results at least partially due to the placement of the PPG unit 220. Accordingly, the disclosed embodiments allow for overcoming challenges in performing measurements faced by existing solutions.

The PPG unit 200 may further include a data port 220 for outputting data to be used as described further herein below, which may be connected via data cable 225 to a control circuit, for example but not limited to the control circuit 110 as described with respect to FIG. 1 above. Measurements generated by the PPG unit 200 may be transferred to the control circuit in this manner for further processing or transmission.

Figure 3:
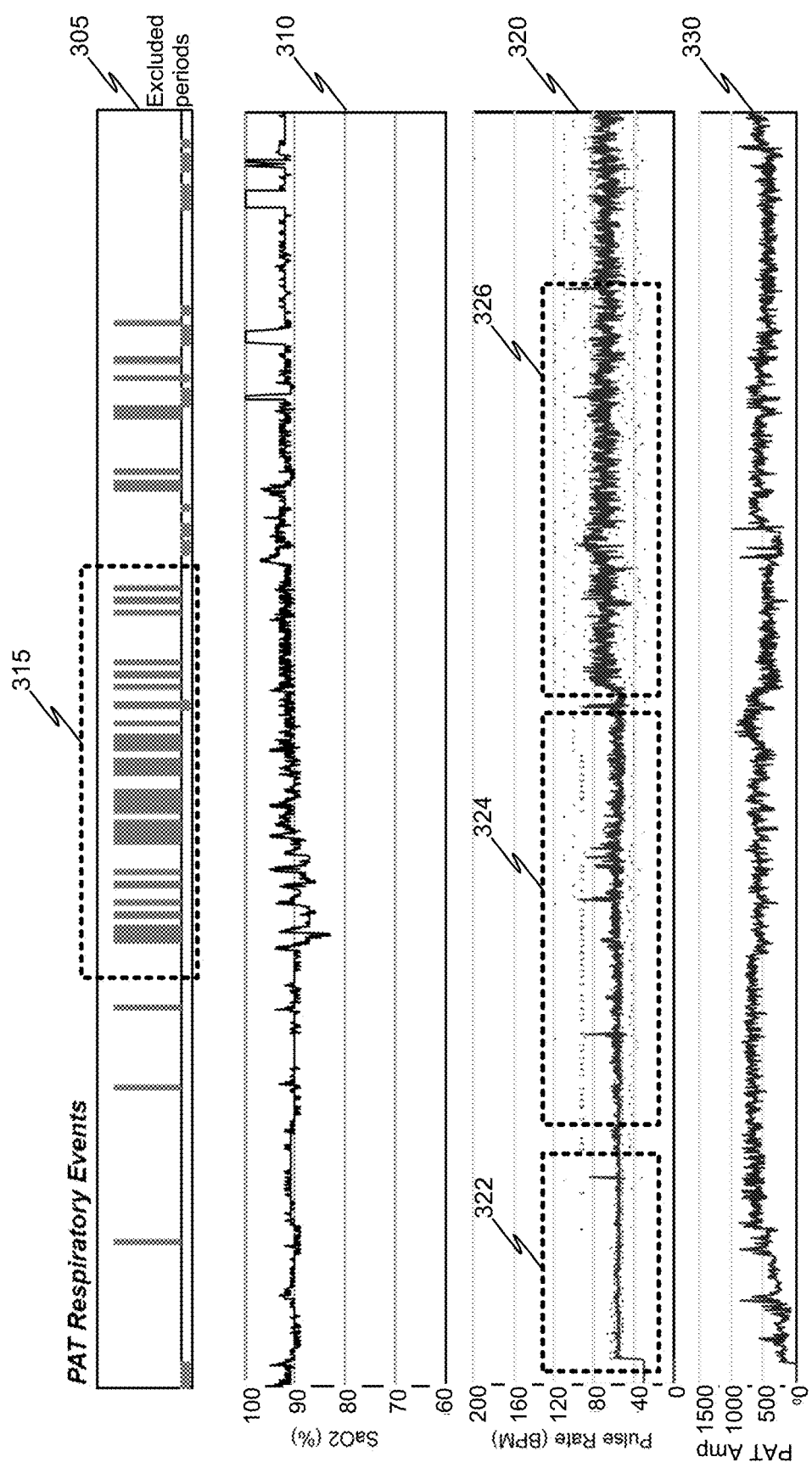
FIG. 3 is a graph result of a sleep study of a patient exhibiting atrial fibrillation (Afib), generated according to an embodiment.

FIG. 3 is a graph result of a sleep study of a patient exhibiting atrial fibrillation (Afib), generated according to an embodiment. The sleep study includes a graph of respiratory events 305, an oxygen saturation graph 310, an average pulse rate graph 320 and a PAT amplitude graph 330.

A graph of respiratory events 305 may be generated based on a received PPG signal, and in this example, a PAT signal which includes a PPG signal is used. In some implementations, the graph is not generated, and respiratory events are logged in a table, database, ledger, or other suitable data structure.

In the example implementation shown in FIG. 3, the average pulse rate graph 320 includes data points generated for a total period of over 200 minutes. The average pulse rate graph 320 further includes a first section 322, a second section 324 and a third section 326. During the first section 322, the patient exhibits a normal pattern expressed by a continuous line and intervals between each heartbeat. Dots surrounding the line represent histogram values. As seen in FIG. 3, the dot pattern is fairly consistent for the first section 322.

During the second section 324, the patient exhibits a normal pattern laced with premature beats. Detection of premature beats is discussed in more detail below.

During the third section 326, the patient exhibits Afib which can be seen both by erratic heartbeats and inconsistent histogram values. The spread of dots is clearly more pronounced in the third section 326.

The detected respiratory events graph 305, which is a result of conducting a sleep study, is beneficial here as there is a correlation between apnea events and arrhythmic events. It is clearly seen in the graphs that there is a plurality of apnea events in time frame 315, indicated by frequent respiratory events, which overlap both the premature heartbeats in the second section 324 and the arrhythmia events of the third section 326 in the average pulse rate graph 320.

Figure 4:
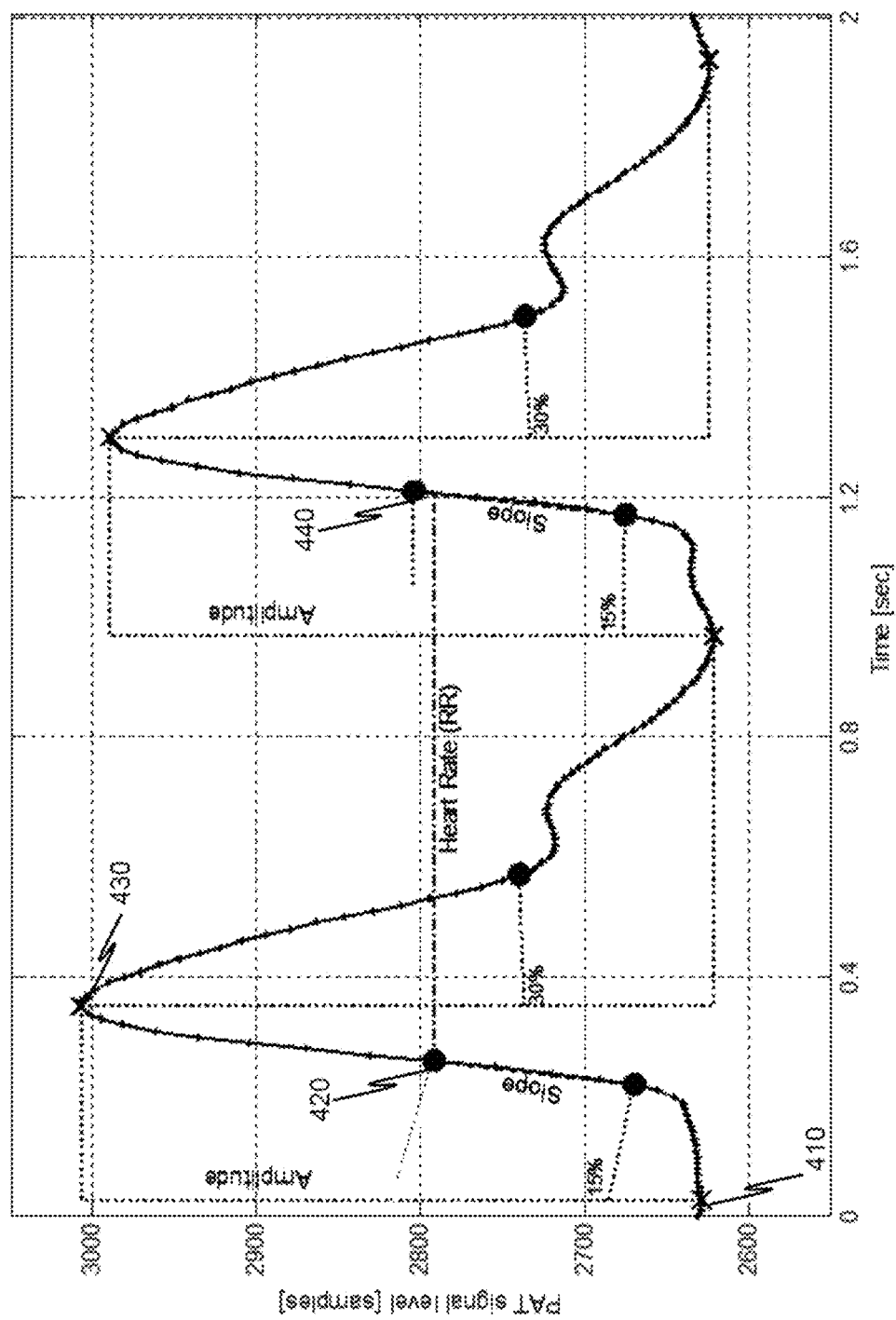
FIG. 4 is a graph of a peripheral arterial tone (PAT) amplitude signal generated according to an embodiment.

FIG. 4 is a graph of a PAT amplitude signal generated according to an embodiment. A PAT signal is generated as described above. In the example implementation shown in FIG. 4, the figure shows a short 2 second interval for simplicity and to discern in detail how an RR interval is determined based on the generated PAT signal. While a PAT signal is used in this embodiment, any PPG signal can be used to determine an RR interval without departing from the scope of the disclosure. An amplitude is determined between a first local minimum point 410 and a first local maximum point 430. In addition, local points indicating 15% of signal amplitude and 30% of signal amplitude are shown in the figure. A first predefined point 420 is determined between the first local minimum point 410 and the first local maximum point 430 of the determined amplitude. A second predefined point 440 is determined for a second amplitude. Each of the predefined points 420 and 440 may have a predetermined value, or may be a predetermined function (e.g., half of the amplitude).

The time period between the first predefined point 420 and the second predefined point 440 corresponds to the RR interval, from which heartbeats per minute (BPM) may be derived.

Figure 5:
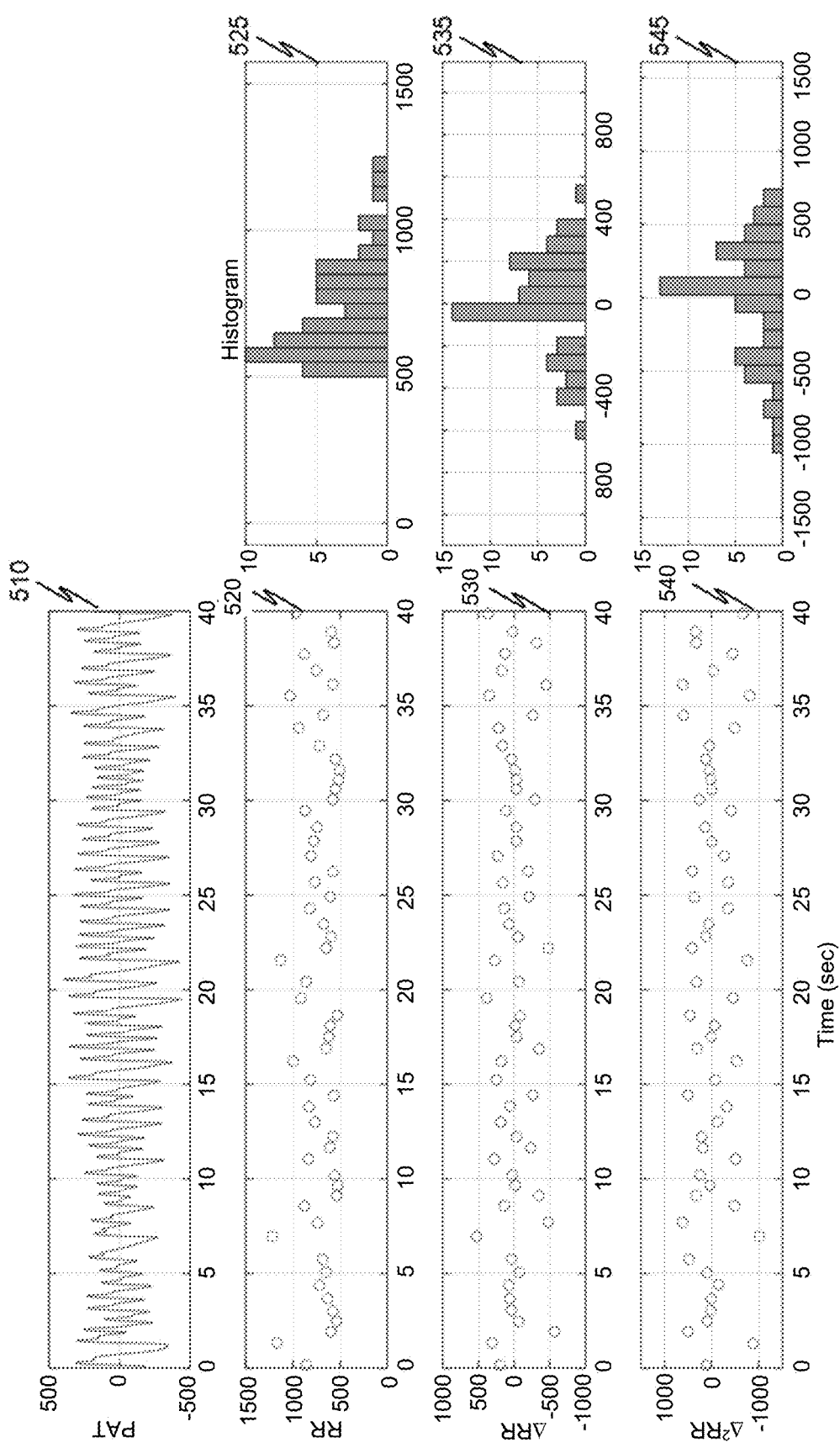
FIG. 5 is a graph of a PAT signal and derived heart rate (RR) interval of a patient exhibiting Afib generated according to an embodiment.

FIG. 5 is a graph of a PAT signal and derived RR interval of a patient exhibiting Afib according to an embodiment. While a PAT signal is described here, a suitable PPG signal may also be used without departing from the scope of the disclosure. In the example implementation shown in FIG. 5, PAT signal graph 510 includes measurements for a time frame of 40 seconds.

RR intervals may be determined based on the PAT signal as described above in FIG. 4 to generate RR graph 520. Delta-RR values are derived as the rate of change of RR intervals to delta-RR graph 530, and delta-delta-RR values are derived as the rate of change between delta-RR values to delta-delta-RR graph 540. For each RR, delta-RR, and delta-delta-RR graph a corresponding histogram 525, 535, 545, respectively, may be generated. It should be apparent that a histogram is one example of estimating a distribution, however other methods for estimating distribution of RR intervals, delta-RR intervals, and delta-delta-RR intervals may be utilized without departing from the scope of this disclosure.

A patient exhibiting Afib is suggested by a wide unimodal distribution for each of the above histograms. By generating these measurements during a sleep apnea test, results may be correlated with sleep apnea events, and the long testing period is further beneficial as results are more stable over time. Further, the likelihood of catching an Afib event increases over the monitored time period.

Figure 6:
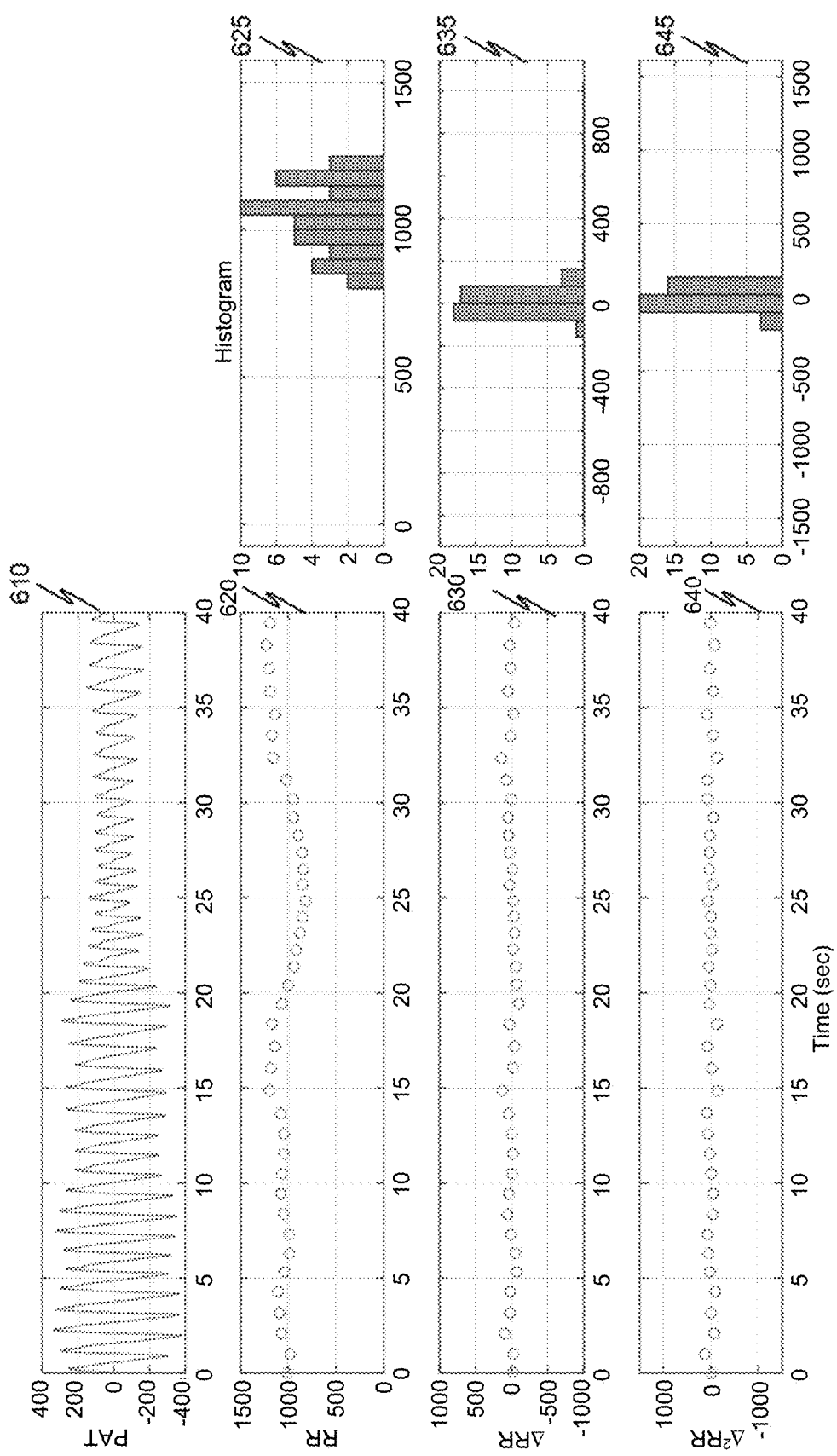
FIG. 6 is a graph of a PAT signal and derived RR interval of a patient exhibiting sleep apnea generated according to an embodiment.

FIG. 6 is a graph of a PAT signal and derived RR interval of a patient exhibiting sleep apnea generated according to an embodiment. While a PAT signal is described here, a suitable PPG signal may also be used. The PAT signal graph 610 includes measurements for a time frame of 40 seconds.

RR intervals may be determined based on the PAT signal as described above to generate RR graph 620. Delta-RR values are derived from the RR intervals (e.g., as the rate of change of RR intervals) to delta-RR graph 630, and delta-delta-RR values are derived from delta-RR (e.g., as the rate of change between delta-RR intervals) to delta-delta-RR graph 640. For each RR, delta-RR, and delta-delta-RR graph, a corresponding histogram (e.g., the histograms 625, 635, and 645, respectively) may be generated.

Figure 7:
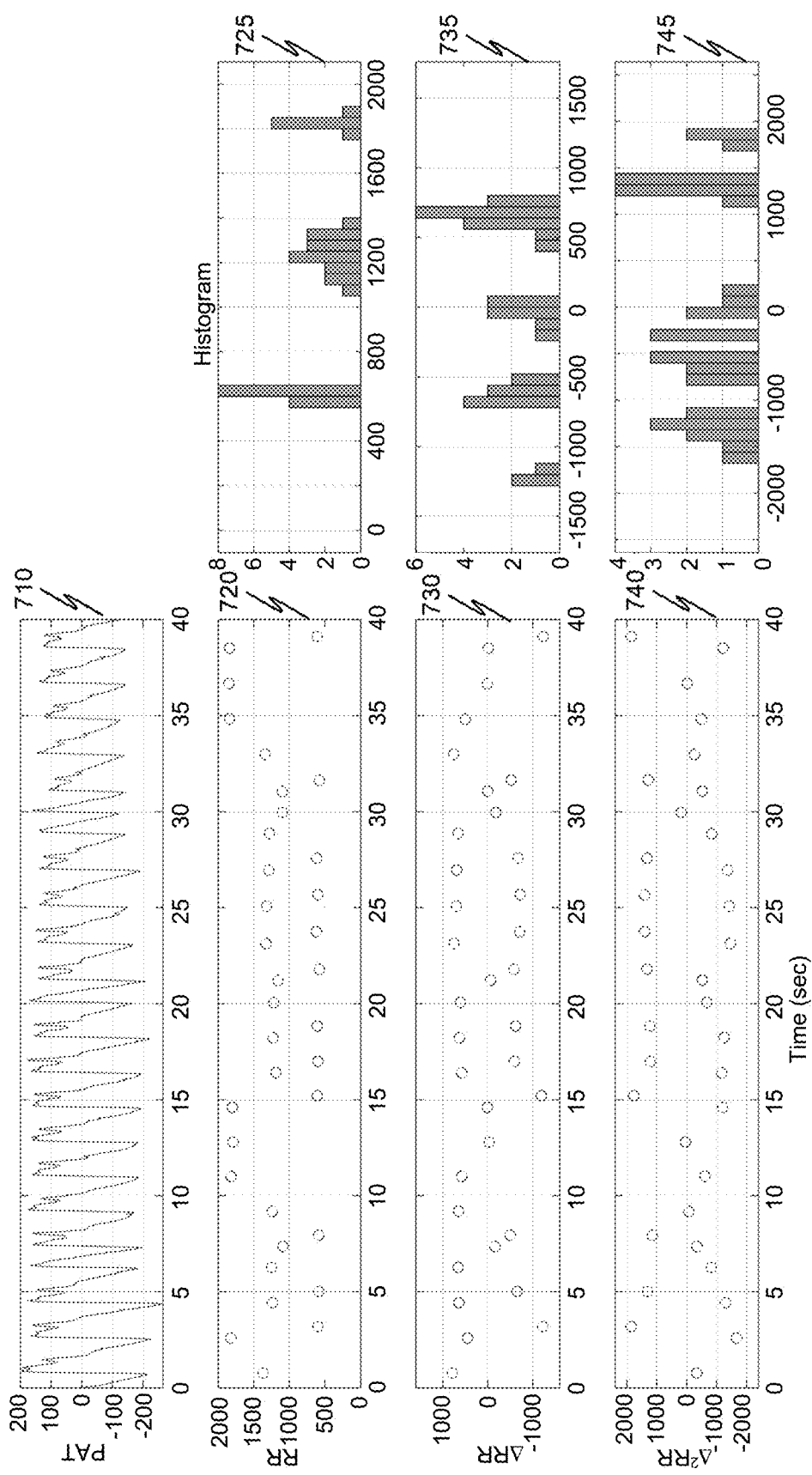
FIG. 7 is a graph of a PAT signal and derived RR interval of a patient exhibiting premature heartbeats according to an embodiment.

FIG. 7 is a graph of a PAT signal and derived RR interval of a patient exhibiting premature heartbeats generated according to an embodiment. While a PAT signal is described here, a suitable PPG signal may also be used without departing from the scope of the disclosure. In the example implementation shown in FIG. 7, the PAT signal graph 710 includes measurements for a time frame of 40 seconds.

RR intervals may be determined based on the PAT signal as described above to generate RR graph 720. Delta-RR values are derived from the RR intervals (e.g., as the rate of change of RR intervals) to delta-RR graph 730, and delta-delta-RR values are derived from delta-RR (e.g., as the rate of change between delta-RR intervals) to delta-delta-RR graph 740. For each RR, delta-RR, and delta-delta-RR graph, a corresponding histogram (e.g., the histograms 725, 735, and 745, respectively) may be generated.

In the case of premature heartbeats, the histograms 725, 735, and 745 will exhibit multimodal distributions. Detection of premature heartbeats is described in more detail below.

A wide distribution may not always be evident. Therefore, it is advantageous to determine a multi-dimensional threshold to what is considered a wide distribution. A feature space of multiple dimensions may be used for the multi-dimensional threshold which includes a width value for each of the RR, delta-RR, and delta-delta-RR histograms, a distance between modalities of any one or more of the histograms, values which are used to determine modalities, and the like.

It has been identified that a single such threshold for all patients does not render accurate results, achieving either high false positive or false negative rates. Therefore, various disclosed embodiments provide a solution for generating more accurate results by using a plurality of potential thresholds and selecting an appropriate threshold for the currently observed patient from the plurality of potential thresholds. In an embodiment, the potential thresholds from which the appropriate threshold is selected are predetermined.

In an embodiment, a threshold is selected such that it produces stable results. In other words, the threshold should be selected so that a change in the value of the threshold that is less than or equal to a predetermined value epsilon ($\varepsilon$) would still result in similar outcomes. In an embodiment, outcomes for modified thresholds are similar if at least a threshold number or proportion of tests run using the threshold before and after modifications result in the same outcome (e.g., outcomes such as detection of an Afib or lack of detection of an Afib). If a small change in the threshold value produces varying outcomes, then the threshold is not suitable for the current patient. In an embodiment, the multi-dimensional threshold may be selected at the conclusion of the sleep test, based on some or all of the generated PPG signals.

In an embodiment, detection of an Afib event may be based on a confidence level of detection. The confidence level may be based on the detection threshold. The confidence level may be also affected by results of the sleep apnea test occurring simultaneously. For example, if an Afib event is suspected, and a sleep apnea event is detected, then the confidence level for detecting the Afib event may rise, as it is more likely to occur in correlation with an apnea event as shown above. A sleep apnea event may be detected from the PPG signal, or from any other sensor of the sleep apnea test, such as an oximetry, chest sensor, positional sensor, acoustic sensor, actigraph, and the like.

Figure 8:
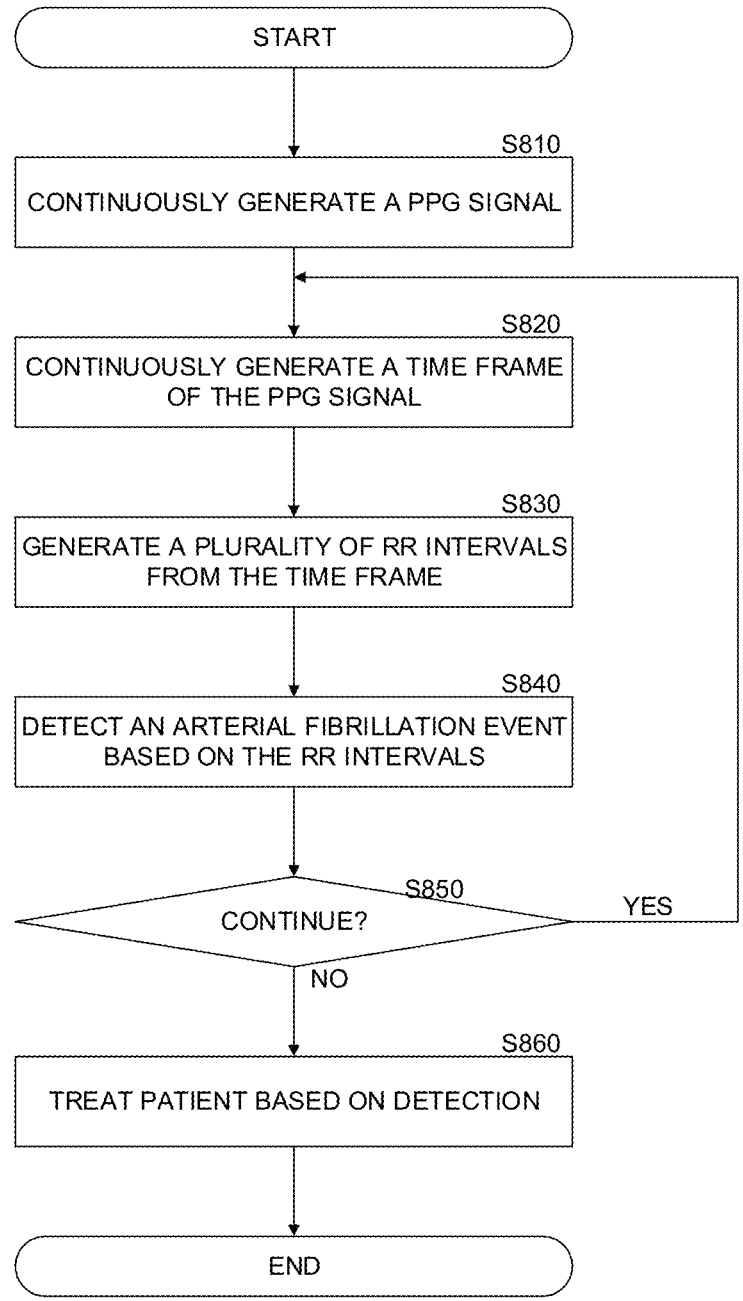
FIG. 8 is a flowchart of a method for detection of atrial fibrillation based on a PPG signal according to an embodiment.

FIG. 8 is a flowchart of a method for detection of Afib based on a PPG signal according to an embodiment. In an embodiment, the method is performed by the PPG unit 100, FIG. 1.

At S810, a PPG signal is generated continuously. The PPG signal may be a PAT signal as described above, in certain embodiments. In some embodiments, multiple PPG signals may be used, for example from different areas of the body (e.g., different fingers, wrists, ears, palms, etc.). It has been identified that it is advantageous to continuously generate a signal as the likelihood of detecting a cardiovascular event increases with continuous monitoring. Therefore, monitoring cardiovascular events while simultaneously conducting a sleep apnea test is beneficial, and can provide additional data and insights from a single exam. Sleep apnea is linked to cardiac conditions such as arrhythmia and, therefore, generating additional information improves patient care.

At S820, a time frame sample is continuously generated from the PPG signal. For example, while the PPG signal is being generated continuously and recorded or transmitted for recording, a control circuit may be configured to analyze the signal for a given time frame. For example, in FIGS. 5 through 7, a 40 second time frame sample was utilized. It should be readily apparent that a sliding time window of 40 seconds is merely one example, and other appropriate values may be used without departing from the scope of the disclosure. In certain embodiments, overlapping or non-overlapping time windows may be utilized.

At S830, a plurality of RR intervals is generated from the time frame samples. The RR intervals may be generated as described above with respect to FIG. 4. Delta-RR intervals, delta-delta-RR intervals, or both, may also be generated.

At S840, an Afib event is detected within the time frame sampled by determining a modality of distribution of RR interval length of at least a portion of the plurality of RR intervals including a first RR interval and a second RR interval. The first and second RR intervals may be, but are not limited to, randomly selected from among the plurality of RR intervals. In an embodiment, an Afib event is detected when the difference in respective lengths of the first and second RR intervals is above a threshold. It should be noted that it is advisable to utilize a plurality of RR intervals and corresponding derivatives, for more accurate results.

In an embodiment, detection of the Afib event further includes determining that the RR intervals, delta-RR intervals, and delta-delta RR intervals each have a unimodal wide distribution. It should be noted that for any 'N' number of RR intervals, there are 'N−1' delta-RR intervals and 'N−2' delta-delta RR intervals. Therefore, accuracy of detection may be improved by selecting at least five RR intervals. Accordingly, in a further embodiment, 5 or more RR intervals are selected.

At S850, a check is performed to determine whether to continue by monitoring the next time frame. In an embodiment, monitoring may continue as long as the sleep apnea test continues, e.g., until a predetermined period of time has passed, until a patient wakes up, until sensors are removed from the patient, and the like. If 'yes,' execution may continue at S820; otherwise, execution may continue with S860.

At S860, the patient is treated based on any detected Afib events. In an embodiment, S860 may include electrical cardioversion or prescribing a drug regimen cardioversion. Certain anti-arrhythmics, such as Dofetilide, may restore a normal sinus rhythm. Long term care may involve prescribing beta blockers to slow down a patient's heart rate. In certain cases, a procedure of left atrial appendage closure may be performed as part of the treatment. Such a procedure may include guiding a catheter through a vein in the patient's leg to the left atrium and inserting a device through the catheter to close an appendage in the left atrium. This may reduce the risk of blood clots, which tend to form in the left atrial appendage. Patients who do not suffer heart valve problems, who have an increased risk of blood clots and bleeding, or who are unable to take anticoagulants are candidates for this type of procedure.

Figure 9:
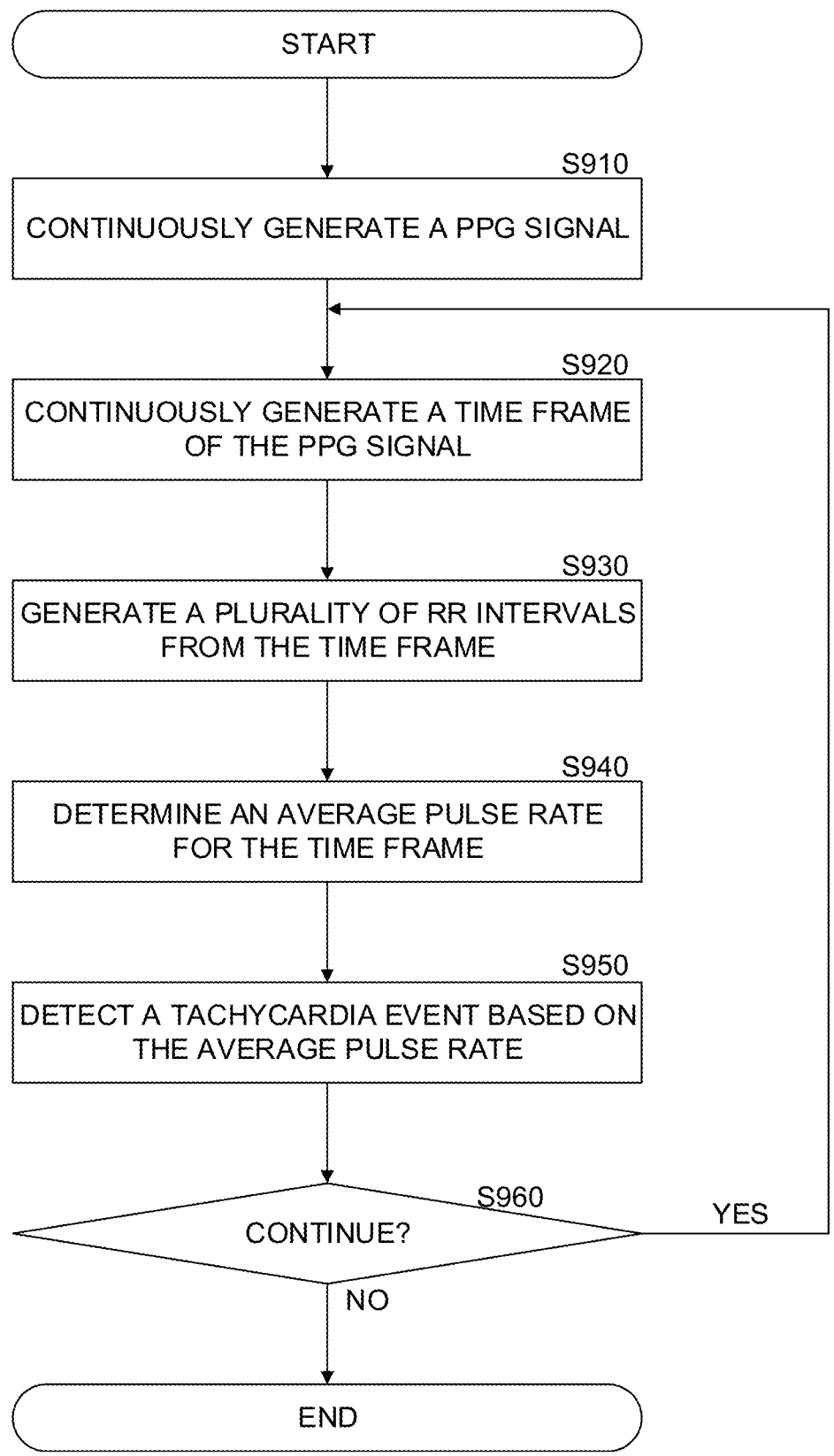
FIG. 9 is a flowchart of a method for detecting tachycardia events from a PPG signal according to an embodiment.

FIG. 9 is a flowchart of a method for detecting tachycardia events from a PPG signal according to an embodiment. In an embodiment, the method is performed by the PPG unit 100, FIG. 1.

At S910, a PPG signal is generated continuously. The PPG signal may be a PAT signal as described above, in certain embodiments. In some embodiments, multiple PPG signals may be used, for example from different areas of the body (e.g., different fingers, wrists, ears, palms, etc.). It has been identified that it is advantageous to continuously generate a signal for monitoring as the likelihood of detecting a cardiovascular event increases. Therefore, monitoring cardiovascular events while simultaneously conducting a sleep apnea test is beneficial, and can provide additional data and insights from a single exam.

At S920, a time frame sample is continuously generated from the PPG signal. For example, while the PPG signal is being generated continuously and recorded or transmitted for recording, a control circuit (e.g., the control circuit 110, FIG. 1) may be configured to analyze the signal for a given time frame. For example, in FIGS. 5 through 7, a 40 second time frame sample was utilized. It should be readily apparent that the sliding time window of 40 seconds is merely one example, and other appropriate values may be used.

At S930, a plurality of RR intervals is generated from the PPG signal. The RR intervals may be generated as described above.

At S940, an average pulse rate is determined for the time frame, based on the RR intervals.

At S950, a tachycardia event is detected within the time frame sample, by determining that a segment of the time frame includes RR intervals indicating heartbeats exceeding a predetermined threshold value. Tachycardia is typically defined as exceeding 100 BPM for a sustained period of time, or exceeding 90 BPM during sleep. To this end, in an embodiment, the predetermined threshold value indicates 100 BPM average pulse rate over at least a predetermined period of time while the patient is awake. In another embodiment, the predetermined threshold value indicates 90 BPM for a predefined time length or a predefined number of beats (e.g. 10 beats) at any point while the patient is asleep.

At S960, a check is performed to determine if to continue by monitoring the next time frame. In an embodiment, monitoring may continue as long as the sleep apnea test continues, e.g., until a predetermined period of time has passed, until a patient wakes up, until sensors are removed from the patient, and the like. If 'yes' execution may continue at S920; otherwise, execution may terminate.

Figure 10:
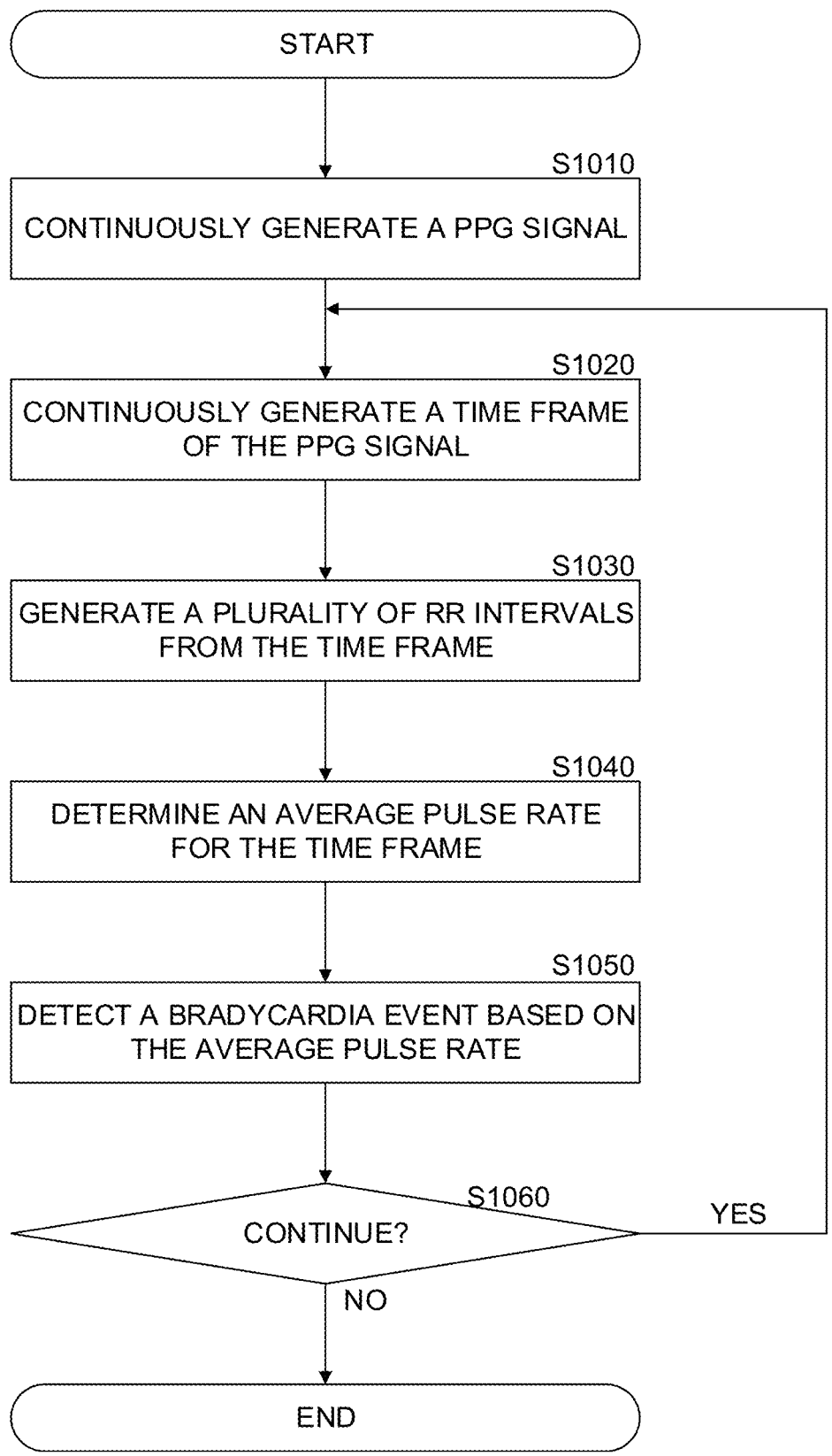
FIG. 10 is a flowchart of a method for detecting bradycardia events from a PPG signal according to an embodiment.

FIG. 10 is a flowchart of a method for detecting bradycardia events from a PPG signal according to an embodiment. In an embodiment, the method is performed by the PPG unit 100, FIG. 1.

At S1010, a PPG signal is generated continuously. The PPG signal may be a PAT signal as described above, in certain embodiments. In some embodiments, multiple PPG signals may be used, for example from different areas of the body (e.g., different fingers, wrists, ears, palms, etc.). It has been identified that it is advantageous to continuously generate a signal for monitoring as the likelihood of detecting a cardiovascular event increases. Therefore, monitoring cardiovascular events while simultaneously conducting a sleep apnea test is beneficial, and can provide additional data and insights from a single exam.

At S1020, a time frame sample is continuously generated from the PPG signal. For example, while the PPG signal is being generated continuously and recorded or transmitted for recording, a control circuit may be configured to analyze the signal for a given time frame. For example, in FIGS. 5 through 7, a 40 second time frame sample was utilized. It should be readily apparent that the sliding time window of 40 seconds is merely one example, and other appropriate values may be used.

At S1030, a plurality of RR intervals is generated from the PPG signal. The RR intervals may be generated as described above.

At S1040, an average pulse rate is determined for the time frame, based on the RR intervals.

At S1050, a bradycardia event is detected within the time frame sample, by determining that a segment of the time frame includes RR intervals indicating heartbeats less than a predetermined threshold value (e.g., by having an average pulse rate less than the threshold value for the given time frame). In healthy adults, bradycardia is usually defined as fewer than 60 BPM for a sustained period of time, and fewer than 40 BPM during sleep. To this end, in an embodiment, the predetermined threshold value indicates 60 BPM average pulse rate over at least a predetermined period of time while the patient is awake. In another embodiment, the predetermined threshold value indicates 40 BPM for a predefined time length or a predefined number of beats at any point while the patient is asleep.

At S1060, a check is performed to determine whether to continue by monitoring the next time frame. In an embodiment, monitoring may continue as long as the sleep apnea test continues, e.g., until a predetermined period of time has passed, until a patient wakes up, until sensors are removed from the patient, and the like. If 'yes,' execution may continue at S1020, otherwise execution may terminate.

Figure 11:
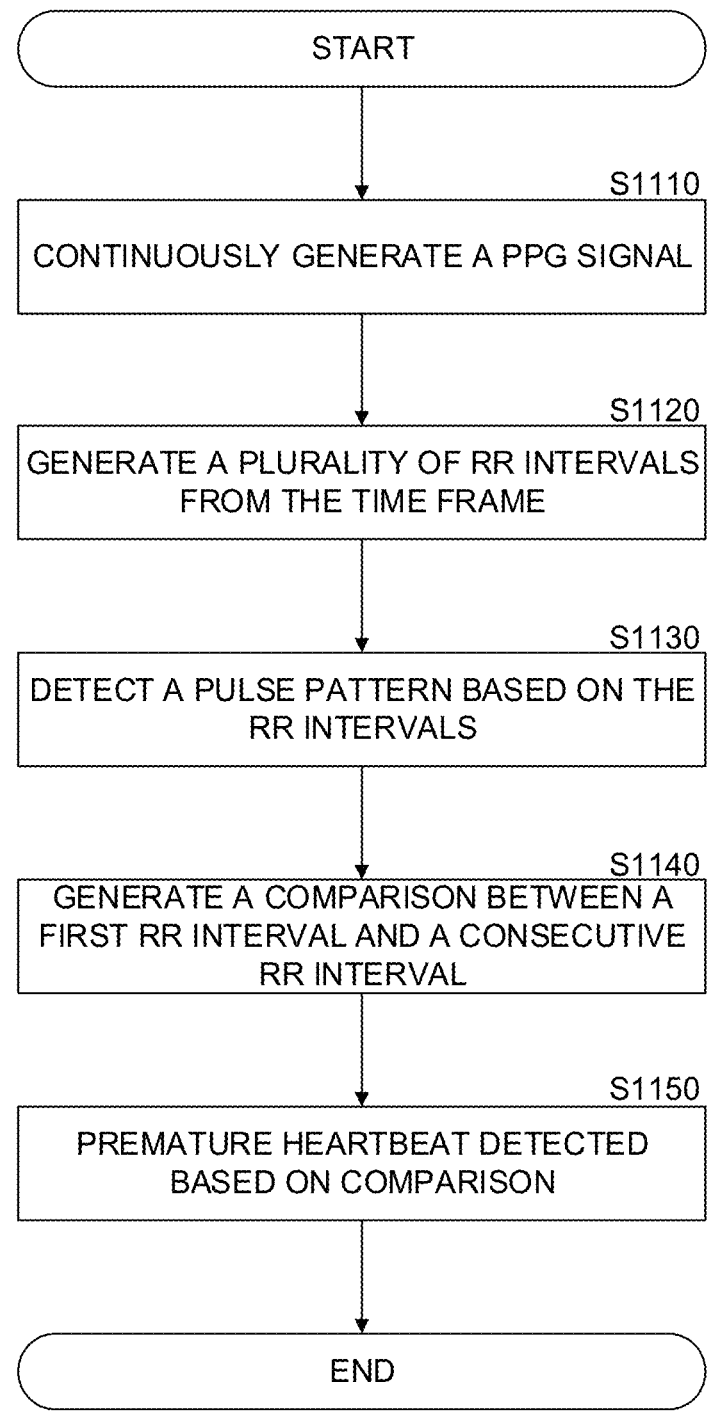
FIG. 11 is a flowchart of a method for detecting premature heartbeats from a PPG signal according to an embodiment.

FIG. 11 is a flowchart of a method for detecting premature heartbeats from a PPG signal according to an embodiment. In an embodiment, the method is performed by the PPG unit 100, FIG. 1.

At S1110, a PPG signal is generated continuously. The PPG signal may be a PAT signal as described above, in certain embodiments. In some embodiments, multiple PPG signals may be used, for example from different areas of the body (e.g., different fingers, wrists, ears, palms, etc.). It has been identified that it is advantageous to continuously generate a signal for monitoring as the likelihood of detecting a cardiovascular event increases. Therefore, monitoring cardiovascular events while simultaneously conducting a sleep apnea test is beneficial, and can provide additional data and insights from a single exam.

At S1120, a plurality of RR intervals is generated from the PPG signal. The RR intervals may be generated as described above.

At S1130, a pulse pattern is detected based on the RR intervals. A pulse pattern includes a plurality of RR intervals, mapped as a function of amplitude over time. Amplitude may represent an amount of blood detected in a blood vessel. Detecting a pulse pattern may include generating a measurement of time between a peak of a first interval and a second interval. A pattern emerges when a plurality of measurements is generated.

At S1140, a comparison is generated between a first RR interval and a consecutive second RR interval. In an embodiment, a further indication of a premature heartbeat may be determined by detecting a reduced amplitude from the first RR interval to the second RR interval (i.e., the second RR interval has a lower amplitude as compared to the first RR interval). In some embodiments, S1140 may further include comparing the first RR interval and the second RR interval to the pulse pattern detected at S1130 in order to identify an interval which is abnormal. Abnormal intervals may be defined by peaks or valleys which deviate (e.g., by at least a threshold value) from the average of the values represented by the peak or valley of the other intervals.

At S1150, it is determined if a premature heartbeat is detected based on the generated comparison. A premature heartbeat may be detected by determining that: the first RR interval is shorter than each of a plurality of RR intervals of the same time frame, and that the second RR interval is within a predefined threshold of each of the plurality of RR intervals (i.e., is similar to the other RR intervals of the time frame or longer).

In an embodiment, a premature heartbeat may be further detected by determining that an RR interval exceeds a threshold. The threshold may be determined based on a plurality of RR intervals in a same time frame as the first RR interval.

In some embodiments, a chest sensor or actigraphy unit that detects patient movement may be further used to determine whether the PPG signal is reliable, where an anomalous RR interval may indicate movement exhibited by the patient such that any anomalous RR intervals are further analyzed with respect to outputs of the chest sensor or actigraphy unit to determine whether they represent a reliable signal or a patient movement (and, therefore, can be excluded). In certain embodiments, a snore sensor (such as a microphone or piezo sensor) may be used to determine that the PPG signal is reliable by indicating that the patient exhibits normal snore rate levels.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for evaluation of sleep disordered breathing and atrial fibrillations of a patient based on analysis of a photoplethysmogram (PPG) signal, comprising:
    applying a static pressure field to a digit of the patient;
    during application of the static pressure field to the digit, continuously generating PPG signal measurements from a sensor of a PPG unit applied to the digit of the patient;
    generating a plurality of time frame samples based on the PPG signal measurements;
    generating, for each time frame sample, a plurality of heart rate (RR) intervals;
    determining an RR interval distribution for each time frame sample based on the plurality of RR intervals;
    detecting at least one atrial fibrillation event based on the RR interval distribution for each time frame sample;
    detecting at least one sleep disordered breathing event based at least in part on the generated PPG signal measurements from the sensor of the PPG unit during the application of the static pressure field; and
    generating a sleep report comprising a visual indication of the at least one sleep disordered breathing event and a visual indication of the at least one atrial fibrillation event.

2. The method of claim 1, further comprising:
    generating a plurality of delta RR values based on the plurality of RR intervals, wherein the at least one atrial fibrillation event is detected based further on the plurality of delta RR values.

3. The method of claim 2, further comprising:
    generating a plurality of delta-delta RR values based on the plurality of delta RR values, wherein the at least one atrial fibrillation event is detected based further on the plurality of delta-delta RR values.

4. The method of claim 3, further comprising:
    determining a delta RR value distribution of delta RR values and a delta-delta RR value distribution of delta-delta RR values, wherein the at least one atrial fibrillation event is detected based further on the delta RR value distribution and the delta-delta RR value distribution, and wherein each determined distribution is a wide unimodal distribution indicating atrial fibrillation in a patient.

5. The method of claim 1, further comprising:
    selecting a multi-dimensional threshold from a plurality of multi-dimensional threshold values, wherein the selected multi-dimensional threshold is selected based on the continuously generated PPG signal measurements, and wherein the at least one atrial fibrillation event is detected based further on the selected multi-dimensional threshold.

6. The method of claim 1, wherein the generated sleep report represents a predetermined time window, and wherein the sleep report includes at least one of: a respiratory events graph, an oxygen saturation graph, a pulse rate graph, or a pulse wave PAT amplitude graph.

7. The method of claim 1, further comprising:
    generating an actigraphy signal; and
    determining a state of either sleep or awake based on the actigraphy signal, wherein the sleep report further includes the determined state.

8. The method of claim 1, further comprising:
    generating at least one of: a chest sensor signal, a positional sensor signal, or a snore sensor signal; and
    determining at least one of: a body position based on the chest sensor signal or positional sensor, or a snore rate based on the snore sensor signal,
    wherein the sleep report further includes the determined at least one of body position and snore rate.

9. A non-transitory computer readable medium having stored thereon instructions for causing a processing circuitry to execute a process for evaluating sleep disordered breathing and atrial fibrillations of a patient based on analysis of a photoplethysmogram (PPG) signal, the process comprising:
    during application of a static pressure field to a digit of a patient, continuously generating PPG signal measurements from a sensor of a PPG unit applied to the digit of the patient;
    generating a plurality of time frame samples based on the PPG signal measurements;
    analyzing the plurality of time frame samples of the PPG signal measurements to detect at least one sleep disordered breathing event occurring during a time represented by the plurality of time frame samples, wherein the detection of the at least one sleep disordered breathing event is based at least in part on the PPG signal measurements from the sensor of the PPG unit during the application of the static pressure field;
    generating, for each time frame sample, a plurality of heart rate (RR) intervals;
    determining an RR interval distribution for each time frame sample based on the plurality of RR intervals;
    detecting at least one atrial fibrillation event based on the RR interval distribution for each time frame sample; and
    generating a sleep report comprising a visual indication of the at least one sleep disordered breathing event and a visual indication of the at least one atrial fibrillation event.

10. The non-transitory computer readable medium of claim 9, wherein the visual indication of the at least one sleep disordered breathing event and the visual indication of the at least one atrial fibrillation event in the generated sleep report indicate a temporal correlation between the at least one sleep disordered breathing event and the at least one atrial fibrillation event.

11. The non-transitory computer readable medium of claim 9, wherein the visual indication of the at least one sleep disordered breathing event comprises a graph of respiratory events for one or more of the plurality of time frame samples and the visual indication of the at least one atrial fibrillation event comprises an average pulse rate graph for the one or more of the plurality of time frame samples.

12. The non-transitory computer readable medium of claim 11, wherein the one or more of the plurality of time frame samples of the graph of respiratory events are vertically aligned with the one or more of the plurality of time frame samples of the average pulse rate graph in the generated sleep report.

13. The non-transitory computer readable medium of claim 9, wherein the process further comprises determining a state of either sleep or awake of a patient based on a heart rate of the patient determined based on the PPG signal measurements, and wherein the process comprises generating the sleep report based on PPG signal measurements generated for times when the patient is determined to be in the state of sleep.

14. A system for evaluation of sleep disordered breathing and atrial fibrillations (Afib) of a patient based on analysis of a photoplethysmogram (PPG) signal, comprising:
- a probe housing configured to generate a static pressure field to a digit of the patient placed in the probe housing;
- at least one PPG sensor disposed in the probe housing configured to generate PPG signal measurements associated with the digit of the patient during sleep;
- an output interface;
- a processing circuitry in communication with the at least one PPG sensor and the output interface; and
- a memory, the memory containing instructions that, when executed by the processing circuitry, configure the system to:
  - during application of the static pressure field to the digit, continuously generate PPG signal measurements from the at least one PPG sensor;
  - generate a plurality of time frame samples based on the PPG signal measurements;
  - analyze the plurality of time frame samples of the PPG signal measurements to detect at least one sleep disordered breathing event occurring during a time represented by the plurality of time frame samples, wherein the detection of the at least one sleep disordered breathing event is based at least in part on the generated PPG signal measurements from the at least one PPG sensor disposed in the probe housing during the application of the static pressure field;
  - generate, for each time frame sample, a plurality of heart rate (RR) intervals;
  - determine an RR interval distribution for each time frame sample based on the plurality of RR intervals;
  - detect at least one atrial fibrillation event based on the RR interval distribution for each time frame sample; and
  - cause the output interface to provide a sleep report comprising a visual indication of the at least one sleep disordered breathing event and a visual indication of the at least one atrial fibrillation event.

15. The system of claim 14, wherein the system is further configured to:
- generate a plurality of delta RR values based on the plurality of RR intervals, wherein the at least one atrial fibrillation event is detected based further on the plurality of delta RR values.

16. The system of claim 14, wherein the system is further configured to:
- select a multi-dimensional threshold from a plurality of multi-dimensional threshold values,
- wherein the selected multi-dimensional threshold is selected based on the continuously generated PPG signal measurements, and
- wherein the at least one atrial fibrillation event is detected based further on the selected multi-dimensional threshold.

17. The system of claim 14, wherein the sleep report represents a predetermined time window, wherein the sleep report includes at least one of: a respiratory events graph, an oxygen saturation graph, a pulse rate graph, or a pulse wave PAT amplitude graph.

18. The system of claim 14, wherein the system is further configured to:
- generate an actigraphy signal; and
- determine a state of either sleep or awake based on the actigraphy signal, wherein the sleep report further includes the determined state.

19. The system of claim 14, wherein the system is further configured to:
- generate at least one of: a chest sensor signal, a positional sensor signal, or a snore sensor signal; and
- determine at least one of: a body position based on the chest sensor signal or positional sensor, or a snore rate based on the snore sensor signal,
- wherein the sleep report further includes the determined at least one of the body position or the snore rate.

20. The system of claim 14, wherein the visual indication of the at least one sleep disordered breathing event and the visual indication of the at least one atrial fibrillation event in the sleep report indicate a temporal correlation between the at least one sleep disordered breathing event and the at least one atrial fibrillation event.

21. The system of claim 14, wherein the visual indication of the at least one sleep disordered breathing event comprises a graph of respiratory events for one or more of the plurality of time frame samples and the visual indication of the at least one atrial fibrillation event comprises an average pulse rate graph for the one or more of the plurality of time frame samples.

22. The system of claim 21, wherein the one or more of the plurality of time frame samples of the graph of respiratory events are vertically aligned with the one or more of the plurality of time frame samples of the average pulse rate graph in the sleep report.

23. The system of claim 14, wherein the probe housing is configured to generate a static uniform pressure field that prevents free venous flow due to hydrostatic pressure, while allowing veins of the patient to carry blood delivered by arteries out of the digit.

24. The system of claim 14, wherein the instructions, when executed by the processing circuitry, cause the system to determine a state of either sleep or awake of the patient based on a heart rate of the patient determined based on the PPG signal measurements, and wherein the sleep report is generated based on PPG signal measurements generated for times when the patient is determined to be in the state of sleep.

25. A system for detecting atrial fibrillations (Afib) from a photoplethysmogram(PPG) signal, comprising:
- at least one PPG sensor configured to detect PPG signal measurements for a patient during sleep;
- an output interface;
- a processing circuitry in communication with the at least one PPG sensor and the output interface; and
- a memory, the memory containing instructions that, when executed by the processing circuitry, configure the system to:
  - continuously generate PPG signal measurements from the at least one PPG sensor;
  - generate a plurality of time frame samples based on the PPG signal measurements;
  - generate, for each time frame sample, a plurality of heart rate (RR) intervals;
  - determine an RR interval distribution for each time frame sample based on the plurality of RR intervals;
  - generate a plurality of delta RR values based on the plurality of RR intervals;
  - generate a plurality of delta-delta RR values based on the plurality of delta RR values;
  - detect at least one atrial fibrillation event based on the plurality of delta-delta RR values; and
  - cause the output interface to provide a report comprising an indication of the detected at least one atrial fibrillation event.

26. The system of claim 25, wherein the system is further configured to:
- determine a delta RR value distribution of delta RR values and a delta-delta RR value distribution of delta-delta RR values,
- wherein the at least one atrial fibrillation event is detected based further on the delta RR value distribution and the delta-delta RR value distribution, and
- wherein each determined distribution is a wide unimodal distribution indicating atrial fibrillation in a patient.

* * * * *